United States Patent
Inoue et al.

(10) Patent No.: US 12,387,334 B2
(45) Date of Patent: Aug. 12, 2025

(54) ULTRASOUND DIAGNOSTIC APPARATUS AND ULTRASOUND IMAGE PROCESSING METHOD

(71) Applicant: FUJIFILM Healthcare Corporation, Kashiwa (JP)

(72) Inventors: Kenta Inoue, Chiba (JP); Takehiro Tsujita, Chiba (JP); Tomofumi Nishiura, Chiba (JP); Yoko Horie, Chiba (JP); Maki Kuwayama, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 456 days.

(21) Appl. No.: 17/970,433

(22) Filed: Oct. 20, 2022

(65) Prior Publication Data

US 2023/0196580 A1    Jun. 22, 2023

(30) Foreign Application Priority Data

Dec. 17, 2021    (JP) ................. 2021-204742

(51) Int. Cl.
| | |
|---|---|
| G06T 7/00 | (2017.01) |
| A61B 8/00 | (2006.01) |
| A61B 8/08 | (2006.01) |
| G06T 7/73 | (2017.01) |
| G06T 11/20 | (2006.01) |
| G16H 30/40 | (2018.01) |

(52) U.S. Cl.
CPC ............ *G06T 7/0016* (2013.01); *A61B 8/085* (2013.01); *A61B 8/463* (2013.01); *A61B 8/469* (2013.01); *G06T 7/74* (2017.01); *G06T 11/206* (2013.01); *G16H 30/40* (2018.01); *G06T 2207/10016* (2013.01); *G06T 2207/10132* (2013.01); *G06T 2207/20076* (2013.01); *G06T 2207/30096* (2013.01); *G06T 2210/41* (2013.01)

(58) Field of Classification Search
CPC ....... G06T 7/0016; G06T 7/74; G06T 11/206; G06T 2207/10016; G06T 2207/10132; G06T 2207/20076; G06T 2207/30096; G06T 2210/41; G16H 30/40; A61B 8/085; A61B 8/463; A61B 8/469
See application file for complete search history.

(56) References Cited

U.S. PATENT DOCUMENTS

| 2012/0136255 A1 | 5/2012 | Fan et al. | |
| 2018/0085088 A1* | 3/2018 | Du ............ | A61B 8/462 |

(Continued)

FOREIGN PATENT DOCUMENTS

| JP | 2004-159739 A | 6/2004 |
| JP | 2020-028680 A | 2/2020 |

(Continued)

OTHER PUBLICATIONS

Japanese official action issued on Nov. 5, 2024 in connection with counterpart Japanese Patent Application No. 2021-204742.

*Primary Examiner* — Shefali D Goradia
(74) *Attorney, Agent, or Firm* — Paul Teng

(57) ABSTRACT

A mark that identifies a lesion site is displayed on a tomographic image. A two-dimensional map and a graph are displayed regardless of whether or not the mark is displayed. The two-dimensional map represents lesion site probability distribution. The graph represents temporal change of lesion site probabilities.

19 Claims, 7 Drawing Sheets

(56) References Cited

U.S. PATENT DOCUMENTS

| | | | |
|---|---|---|---|
| 2018/0249900 A1 | 9/2018 | Imaizumi et al. | |
| 2020/0116630 A1* | 4/2020 | Zhu | G01N 21/474 |
| 2021/0366120 A1 | 11/2021 | Ito et al. | |
| 2021/0398676 A1* | 12/2021 | Evans | G16H 15/00 |
| 2022/0313092 A1* | 10/2022 | Daures | A61B 90/36 |

FOREIGN PATENT DOCUMENTS

| | | |
|---|---|---|
| JP | 2021-185970 A | 12/2021 |
| WO | WO 2011/155168 A1 | 12/2011 |
| WO | WO 2017/081976 A1 | 5/2017 |

\* cited by examiner

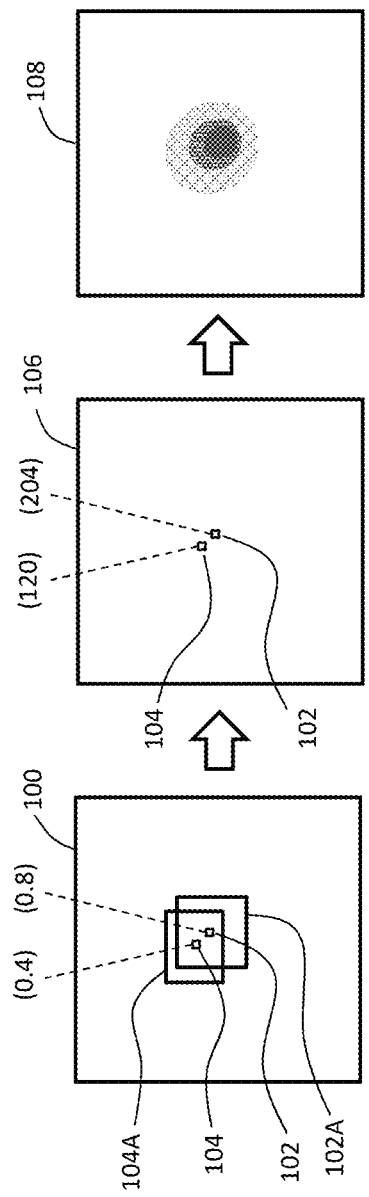
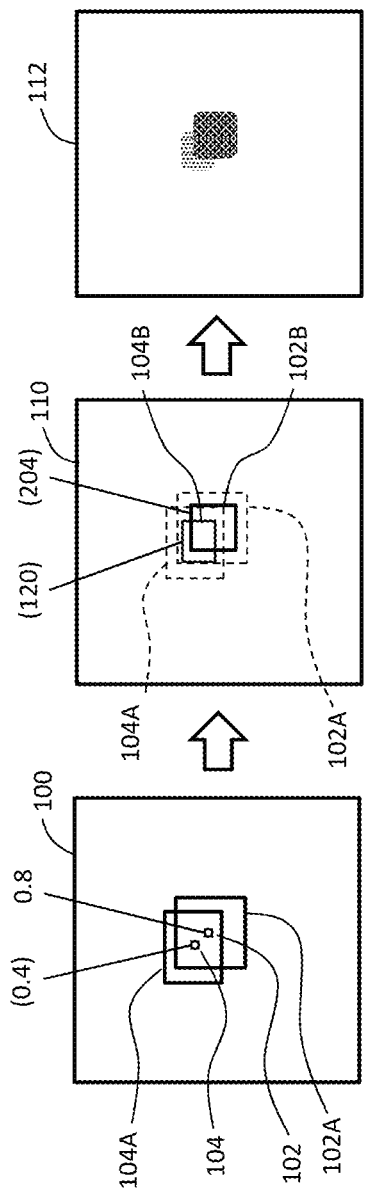

ULTRASOUND DIAGNOSTIC APPARATUS AND ULTRASOUND IMAGE PROCESSING METHOD

CROSS REFERENCE TO RELATED APPLICATION

This application claims priority to Japanese Patent Application No. 2021-204742 filed on Dec. 17, 2021, which is incorporated herein by reference in its entirety including the specification, claims, drawings, and abstract.

TECHNICAL FIELD

The present disclosure relates to an ultrasound diagnostic apparatus and an ultrasound image processing method and, in particular, relates to information generation and presentation for assisting with ultrasound inspection.

BACKGROUND

When performing ultrasound inspection (ultrasonic examination) using an ultrasound diagnostic apparatus, an inspector observes an ultrasound image and simultaneously operates a probe (ultrasound probe). If a lesion site (to be more precise, a lesion site candidate), such as a tumor, appears in the ultrasound image, that lesion site is examined carefully.

Some ultrasound diagnostic apparatuses have a function of automatically detecting a lesion site that has appeared in an ultrasound image and providing notification of the detected lesion site. This function is referred to as CADe (Computer Aided Detection). The CADe technique belongs to or is associated with CAD (Computer Aided Detection and Diagnosis). Typically, while CADe is being performed, a lesion site probability (such as a lesion site score or a lesion site similarity) is calculated, and a shape (mark) enclosing the lesion site is displayed when the lesion site probability exceeds a threshold value. No mark is displayed when the lesion site probability does not exceed the threshold value. Using a threshold value in this manner to control whether or not to display a mark avoids occurrence of a situation in which a mark is frequently displayed on an ultrasound image, or avoids occurrence of a situation in which multiple marks are displayed on an ultrasound image.

Patent Document 1 (JP 2020-28680 A) discloses an ultrasound diagnostic apparatus that has an object detection function. Patent Document 1 does not disclose a technique of displaying spatial distribution of lesion site probabilities or temporal change of lesion site probabilities in the form of a dynamic image.

SUMMARY

Although displaying a mark that provides notification of a lesion site on an ultrasound image enables the inspector to recognize that the lesion site is detected, spatial distribution of lesion site probabilities or temporal change of lesion site probabilities cannot be recognized through that mark. As no mark is displayed when the lesion site probability does not exceed the threshold value, even if something resembling a lesion site is actually detected, information indicative of it is not presented to the inspector. In addition to displaying a mark that provides notification of a lesion site, displaying more detailed information regarding the lesion site in an auxiliary manner is desired.

The present disclosure is directed toward assisting an inspector with probe operation or image observation. In other words, the present disclosure is directed toward displaying, along with a mark, inspection assistance information that is different from the mark. Alternatively, the present disclosure is directed toward providing an inspector with auxiliary information for evaluating a lesion site.

According to one aspect of the present disclosure, there is provided an ultrasound diagnostic apparatus comprising a detector unit configured to perform detection processing for detecting a lesion site in an ultrasound image; a mark generator unit configured to generate a mark based on output information from the detector unit, the mark providing notification of the lesion site; a reference information generator unit configured to generate reference information based on the output information as inspection assistance information that is different from the mark, the reference information representing at least one of spatial distribution of lesion site probabilities and temporal change of lesion site probabilities; and a display configured to display the ultrasound image, the mark, and the reference information in real time.

According to another aspect of the present disclosure, there is provided an ultrasound image processing method comprising performing detection processing for detecting a lesion site in an ultrasound image; generating a mark based on output information that represents a result of execution of the detection processing, the mark providing notification of the lesion site; generating reference information based on the output information as inspection assistance information that is different from the mark, the reference information representing at least one of spatial distribution of lesion site probabilities and temporal change of lesion site probabilities; and displaying the ultrasound image, the mark, and the reference information in real time.

BRIEF DESCRIPTION OF DRAWINGS

Embodiments of the present disclosure will be described based on the following figures, wherein:

FIG. 4 illustrates a first example of a map generation method;

FIG. 5 illustrates a second example of a map generation method;

DESCRIPTION OF EMBODIMENTS

Figure 1:
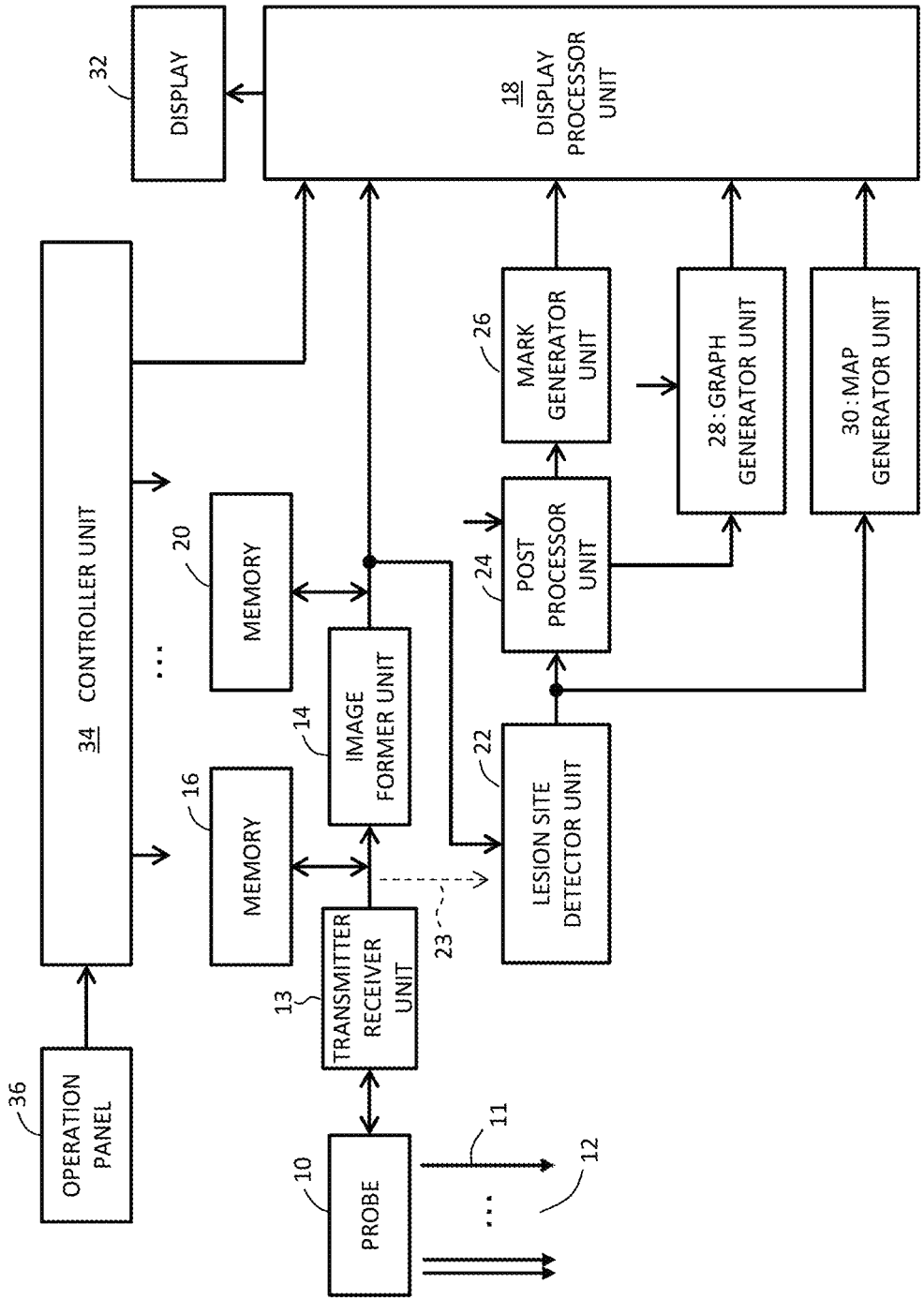
FIG. 1 is a block diagram illustrating an ultrasound diagnostic apparatus according to an embodiment of the present disclosure.

Embodiments of the present disclosure will be described below with reference to the accompanying drawings.

(1) Overview of Embodiments

An ultrasound diagnostic apparatus according to an embodiment of the present disclosure includes a detector unit, a mark generator unit, a reference information generator unit, and a display. The detector unit performs detection processing for detecting a lesion site in an ultrasound image.

The mark generator unit generates a mark based on output information from the detector unit, the mark providing notification of the lesion site. The reference information generator unit generates reference information based on the output information as inspection assistance information that is different from the mark, the reference information representing at least one of spatial distribution of lesion site probabilities and temporal change of lesion site probabilities. The display displays the ultrasound image, the mark, and the reference information in real time.

With the above-described structure, in addition to the mark, the reference information is displayed as inspection assistance information. In an embodiment, the reference information is displayed regardless of whether or not the mark is displayed. Through the observation of the reference image, an inspector can obtain more detailed information regarding a current inspection target (current ultrasound diagnosis target). This enables assistance in careful examination of a lesion site or enables verification of adequacy of mark display. The content of the ultrasound image can be evaluated even under circumstances where no mark is displayed.

In an embodiment, the ultrasound image is a video image (moving image) that shows a current inspection target. A mark is displayed upon detection of a lesion site that satisfies a certain condition. The reference information is a reference image which indicates a response of the detector unit to the current inspection target, and which is a continuously displayed video image. As described above, the ultrasound image, the mark, and the reference information are displayed in real time during ultrasound inspection.

Many items of information or various types of information displayed on the ultrasound image may hinder observation of the ultrasound image. However, presentation of more detailed information other than the mark is needed in order to evaluate the current inspection target in a comprehensive manner or in multiple manners. Therefore, in an embodiment, the mark is displayed on the ultrasound image, and the reference information is displayed in the vicinity of the ultrasound image.

In an embodiment, the reference information generator unit includes a map generator unit that generates, as the reference information, a two-dimensional map that represents spatial distribution of lesion site probabilities. A lesion site can be evaluated in detail through the observation of the two-dimensional map. A site for which notification is not provided can also be evaluated.

In an embodiment, when the output information includes first information that satisfies a mark display condition and second information that does not satisfy the mark display condition, the mark generator unit generates the mark based on the first information, and the map generator unit generates the two-dimensional map based on the first information and the second information. Typically, the mark is displayed intermittently. On the other hand, the two-dimensional map is displayed continuously.

In an embodiment, the reference information generator unit includes a graph generator unit that generates, as the reference information, a graph that represents temporal change of lesion site probabilities. Reference to the graph enables recognition of a lesion site detection frequency or facilitates searching for a lesion site. A plurality of graphs corresponding to a plurality of objects or a plurality of classes may be displayed.

In an embodiment, the graph generator unit identifies, for each frame, a representative value of lesion site probabilities in the frame and generates a graph based on a plurality of representative values identified from a plurality of frames. For example, a representative value for each frame is a maximum value. The frames are reception frames or display frames.

In an embodiment, the mark generator unit generates a mark when the output information satisfies a mark display condition. The mark display condition includes a condition that requires that the lesion site probability identified from the output information exceeds a threshold value. The graph includes a display element that represents the threshold value. The graph generator unit changes the display element in accordance with a change in the threshold value. With this structure, the threshold value can be set with reference to a plurality of representative values.

In an embodiment, the reference information generator unit includes a map generator unit and a graph generator unit. The map generator unit generates a two-dimensional map that represents spatial distribution of lesion site probabilities. The graph generator unit generates a graph that represents temporal change of lesion site probabilities. The reference information includes the two-dimensional map and the graph. With this structure, the inspector's probe operation and image observation can be assisted in a comprehensive manner or in multiple manners.

An ultrasound image processing method according to an embodiment of the present disclosure includes a detection step, a mark generation step, a reference information generation step, and a display step. In the detection step, detection processing for detecting a lesion site in an ultrasound image is performed. In the mark generation step, a mark that provides notification of the lesion site is generated based on output information that represents a result of execution of the detection processing. In the reference information generation step, reference information that represents at least one of spatial distribution of lesion site probabilities and temporal change of lesion site probabilities is generated based on the output information as inspection assistance information that is different from the mark. In the display step, the ultrasound image, the mark, and the reference information are displayed in real time.

The above-described ultrasound image processing method is implemented as software functions or as hardware functions. A program for performing the above-described ultrasound image processing method may be installed onto an information processing apparatus over a network or through a portable storage medium. The concept of the information processing apparatus encompasses an ultrasound diagnostic apparatus, a medical system, a computer, and others. The information processing apparatus includes a non-transitory storage medium.

(2) Details of Embodiments

FIG. 1 illustrates an ultrasound diagnostic apparatus according to an embodiment of the present disclosure. The ultrasound diagnostic apparatus is a medical apparatus for performing ultrasound inspection on a subject (living body) in a healthcare facility or elsewhere. An ultrasound diagnostic apparatus according to an embodiment of the present disclosure has a CADe function, as will be described in detail later; that is, the function of automatically detecting a lesion site included in a tomographic image to provide notification of the lesion site using a mark.

Referring to FIG. 1, a probe 10 is a device for transmitting ultrasound waves to a living body and receiving reflected waves from the living body. More specifically, the probe 10 is composed of a probe head, a cable, and a connector. The probe head is held by an inspector. The probe head is the main component of the probe 10, and in the following description, the probe head is simply referred to as the probe 10.

The probe 10 includes a transducer array that consists of a plurality of transducers. An ultrasound beam 11 is formed by the transducer array, and the ultrasound beam 11 is electronically scanned. Examples of known electronically scanning methods include an electronic linear scanning method and an electronic sector scanning method. A scanning plane 12 is formed by electronically scanning the ultrasound beam 11. The scanning plane 12 is repeatedly formed by repeatedly electronically scanning the ultrasound beam 11. The probe 10 may include a two-dimensional transducer array to obtain volume data from a living body.

A transmitter receiver unit 13 supplies a plurality of transmission signals to the transducer array in parallel with each other during transmission. A transmission beam is formed in this manner. During reception, the transmitter receiver unit 13 performs processing of a plurality of reception signals that are output from the transducer array in parallel with each other. The processing performed here includes A/D conversion processing, phase alignment and summation (delay and summation), and others.

As a result of the processing of the plurality of reception signals, reception beam data are generated. A plurality of sets of reception beam data which are successive in the electronic scanning direction constitute a set of reception frame data. A plurality of sets of reception frame data which are successive on a time axis constitute a reception frame data array. Each set of reception beam data is composed of a plurality of sets of echo data which are successive in the depth direction.

An image former unit 14 is a module that generates a display frame data array based on the reception frame data array. The image former unit 14 has a coordinate conversion function, a pixel interpolation function, a frame rate adjustment function, and other functions. Specifically, the image former unit 14 is composed of a digital scan converter (DSC). Each set of display frame data corresponds to a tomographic image serving as a still-frame image, and the display frame data array corresponds to a tomographic image serving as a video image. An ultrasound image other than a tomographic image may be formed. In an embodiment, the display frame data array is transmitted to a display processor unit 18 and is transmitted to a lesion site detector unit 22. As indicated by reference numeral 23, the reception frame data array may be transmitted to the lesion site detector unit 22.

The reception frame data array may be temporarily stored in a memory 16. Similarly, the display frame data array may be temporarily stored in a memory 20. Each of the memory 16 and the memory 20 serves as a cine memory with a ring buffer structure. In a freeze state (transmission and reception suspend state) after the real-time operation, the frame data arrays stored in the memory 16 and the memory 20 are read.

The lesion site detector unit 22 is composed of a machine learning object detector. Specifically, the lesion site detector unit 22 includes an object detection network (object detection model) such as a CNN, and the object detection network has a plurality of layer sections that are provided in series. The plurality of layer sections perform a plurality of detection steps stepwise. Each of the layer sections includes one or a plurality of convolutional layers and optionally includes one or a plurality of pooling layers. The plurality of detection steps constitute a series of detection processing. Examples of known object detection networks include R-CNN (Regional CNN), SSD (Single Shot MultiBox Detector), M2Det, and YOLO.

In response to input of one tomographic image to the lesion site detector unit 22, output information that is reflective of a feature amount of that tomographic image is generated. The output information represents a lesion site detection result. The output information is transmitted to a postprocessor unit 24 and a map generator unit 30.

The postprocessor unit 24 performs maximum value determination processing and threshold value processing for each display frame. The output information is information that represents spatial distribution of lesion site probabilities. That is, the output information includes a plurality of lesion site probabilities (lesion site scores) that are arrayed two-dimensionally. The maximum value determination processing determines a maximum value in the plurality of lesion site probabilities. The threshold value processing compares the determined maximum value with a threshold value. When the maximum value exceeds the threshold value, it is determined that a mark that indicates detection of a lesion site is to be displayed. When the maximum value does not exceed the threshold value, no mark is displayed.

The postprocessor unit 24 may apply removal processing. For example, the removal processing may reject a falsely detected lesion site. The maximum value that is determined in the maximum value determination processing is transmitted to a graph generator unit 28. The maximum value that has been subjected to the threshold value processing is transmitted to a mark generator unit 26.

When the mark display condition is satisfied (that is, when the maximum value exceeds the threshold value), the mark generator unit 26 generates, as a mark, a rectangular box enclosing the lesion site based on cell information corresponding to the maximum value. The mark is a graphic element. An image that represents the mark is transmitted to the display processor unit 18. The mark may be always generated to allow the mark to be actually rendered upon determination that the lesion site is to be displayed. In either case, the mark appears on the screen when the mark display condition is satisfied.

The map generator unit 30 generates, for each display frame, a two-dimensional map (two-dimensional color map) that represents spatial distribution of lesion site probabilities based on the output information. A plurality of two-dimensional maps corresponding to a plurality of display frames that are successive in chronological order constitute a two-dimensional map serving as a video image. Information that represents a two-dimensional map serving as a video image is transmitted to the display processor unit 18. This two-dimensional map is a video image corresponding to a tomographic image serving as a video image, and serves as a first reference image that assists with ultrasound inspection.

The graph generator unit 28 generates a graph based on a plurality of maximum values that are successive in chronological order. This graph is a video image representing temporal change of lesion site probabilities, and serves as a second reference image that assists with ultrasound inspection. The plurality of maximum values are a plurality of representative values that are representative of the plurality of two-dimensional maps. A plurality of representative values other than the plurality of maximum values may be used. For example, a plurality of average values may be used. Data that represents the generated graph are transmitted to the display processor unit 18.

The graph generated by the graph generator unit 28 includes a plurality of bars that represent the plurality of maximum values, and a line that represents a threshold value. Information that represents a currently set threshold value is transmitted to the postprocessor unit 24 and the graph generator unit 28 from a controller unit 34, which will be described later.

The display processor unit 18 has an image combiner function, a color calculator function, and other functions. The display processor unit 18 generates a display image that is to be displayed on the screen of a display 32. The display image includes a tomographic image serving as an ultrasound image, a mark that is to be superimposed upon the tomographic image, a two-dimensional map serving as the first reference image, and a graph serving as the second reference image. Each of the tomographic image, the mark, the two-dimensional map, and the graph corresponds to a video image that shows information regarding a current inspection target in real time. In the freeze state, the tomographic image, the mark, the two-dimensional map, and the graph may be displayed in the form of a video image or a still-frame image.

The controller unit 34 is composed of a processor (such as a CPU) that executes a program. The controller unit 34 controls the operation of the components illustrated in FIG. 1. Each of the image former unit 14, the display processor unit 18, the lesion site detector unit 22, the postprocessor unit 24, the mark generator unit 26, the graph generator unit 28, and the map generator unit 30 may be composed of a processor or may be implemented as a function that is performed by, for example, a CPU.

An operation panel 36 is an input device, which includes a plurality of switches, a plurality of knobs, a keyboard, a trackball, and others. The operation panel 36 is used to set the above-described threshold value. The display 32 is composed of, for example, a liquid crystal display or an organic EL display device.

Figure 2:
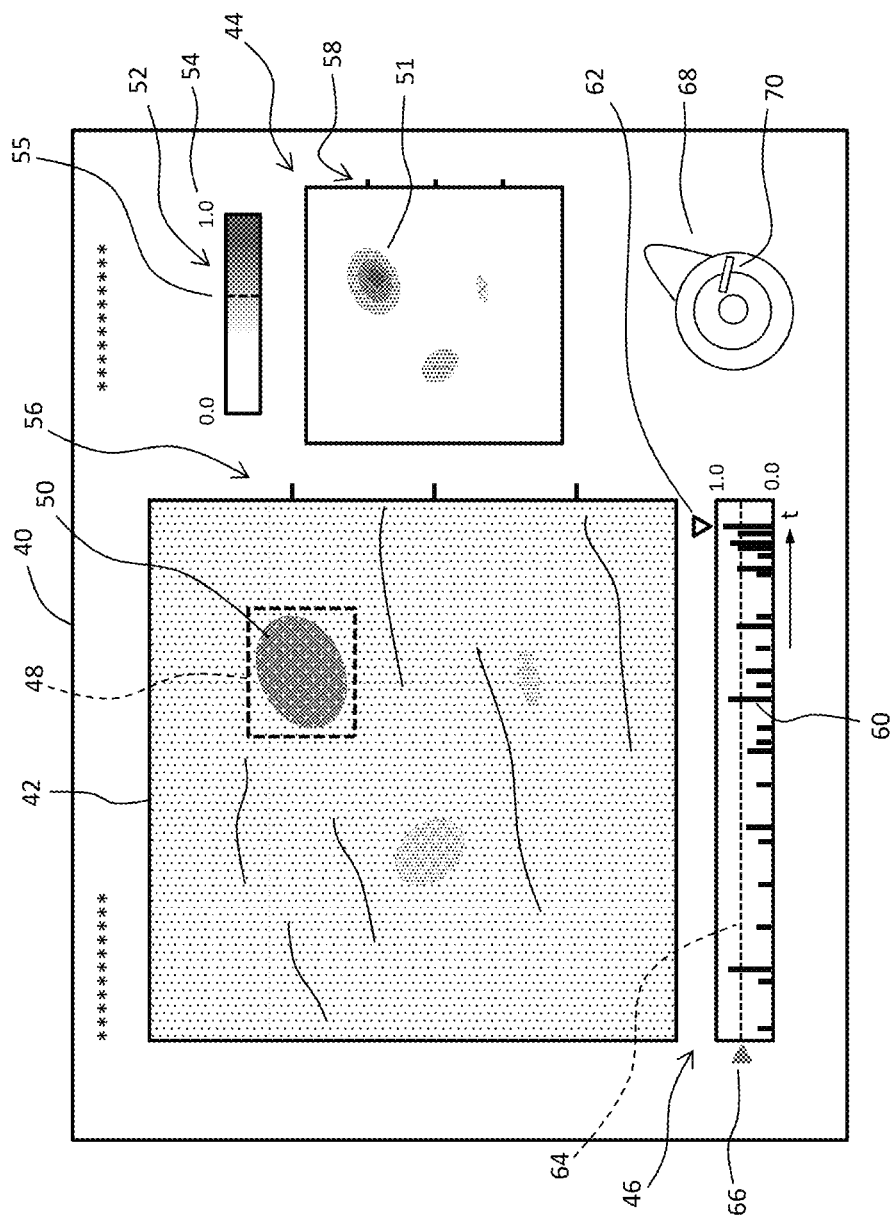
FIG. 2 illustrates an example of a display image.

FIG. 2 illustrates an example of a display image. A display image 40 is displayed on the display screen and includes a tomographic image 42, a two-dimensional map 44, a graph 46, and others.

The tomographic image 42 is a black-and-white image, and a mark 48 that is in the form of a color graphic is superimposed upon the tomographic image 42. In the illustrated example, the tomographic image 42 has a horizontal axis that corresponds to the electronic scanning direction and a vertical axis that corresponds to the depth direction. At the present time, the tomographic image 42 includes a lesion site (specifically, a cross-sectional image of a tumor) 50, and the mark 48 encloses the lesion site 50. Any shape may be used as the mark 48, but the form and the size of the mark 48 are set so as not to hinder observation of the lesion site. The content of the tomographic image 42 changes significantly in accordance with change in the position and the orientation of the probe. A two-dimensional blood flow image may be combined and displayed on the tomographic image 42.

The two-dimensional map 44 represents lesion site probability distribution in a two-dimensional space. The two-dimensional map 44 has a coordinate system corresponding to the coordinate system of the tomographic image 42. In the two-dimensional map 44, the horizontal axis corresponds to the electronic scanning direction, and the vertical axis corresponds to the depth direction. The two-dimensional map 44 shows a scanning plane that is the same as the scanning plane shown by the tomographic image 42. The two-dimensional map 44 is smaller in size than the tomographic image 42, and the two-dimensional map 44 corresponds to a scaled-down image of the tomographic image 42. The two-dimensional map 44 expresses spatial change of lesion site probabilities by the change of hue. Reference numeral 51 denotes a hue-changed portion that corresponds to the lesion site 50 in the tomographic image 42. The two-dimensional map 44 is a video image, and its content changes dynamically in accordance with change in the position and the orientation of the probe.

The tomographic image 42 has depth tick marks 56 along the vertical axis. Correspondingly, the two-dimensional map 44 also has depth tick marks 58 along the vertical axis.

In the illustrated example, the two-dimensional map 44 is displayed on the right side of the tomographic image 42, but it may be displayed on the left side of the tomographic image, above the tomographic image, or below the tomographic image. For convenience in simultaneous observation of the tomographic image 42 and the two-dimensional map 44, they are preferably displayed on the same screen to present the two-dimensional map in the vicinity of the tomographic image 42 so as not to overlap the tomographic image 42.

A color bar 52 is displayed in the vicinity of the two-dimensional map 44. The color bar 52 is a color sample that represents change of hue corresponding to change of lesion site probabilities. In the illustrated example, the color bar 52 is displayed in a manner to have the longitudinal direction of the color bar 52 oriented to be parallel to the horizontal direction. The left end of the color bar 52 corresponds to a lesion site probability of 0.0, and the right end of the color bar 52 corresponds to a lesion site probability of 1.0 (refer to reference numeral 54). A line 55 that represents a currently set threshold value is displayed on the color bar 52. The color bar 52 may also be displayed in a manner in which the longitudinal direction of the color bar 52 is oriented parallel to the vertical direction. In FIG. 2, as the threshold value is changed, the line 55 moves accordingly in the horizontal direction.

The graph 46 represents temporal change of lesion site probabilities. In the graph 46, the horizontal axis corresponds to the time axis, and the vertical axis represents the lesion site probability. The graph 46 is composed of bars 60 that are generated for each display frame, the heights of the bars 60 representing lesion site probabilities. Specifically, the height of each bar 60 represents a maximum value of lesion site probabilities in the display frame. Bars may be displayed at certain time intervals, or maximum values smoothed in the time axis direction may be expressed in the form of a curve. An indicator 62 represents the present time. Although the indicator 62 is displayed at a fixed position, it may be displayed at a position that scans in the horizontal direction.

In addition to a plurality of bars 60, the graph 46 includes a threshold value line 64. The threshold value line 64 represents threshold values that are set at respective times. An indicator 66 represents a current threshold value. When the threshold value is changed using the operation panel, the indicator 66 moves accordingly in the vertical direction. The indicator 66 itself can also be operated, and the threshold value may be changed by moving the indicator 66 in the vertical direction.

In the illustrated display example, a body mark 68 is displayed below the two-dimensional map 44, and a probe mark 70 is also displayed. In an embodiment, diagnosis target organs are breasts, and the body mark 68 schematically illustrates a breast.

Displaying the two-dimensional map 44 and the graph 46 in real time together with a tomographic image including the mark 48 allows the inspector to evaluate a lesion site in a comprehensive manner or in multiple manners. For example, the observation of the two-dimensional map 44 enables recognition of detailed probability distribution regarding a lesion site for which the mark 48 provides notification, or enables recognition of the presence of another lesion site that does not satisfy the mark display condition. The observation of the graph 46 enables recognition of a lesion site detection frequency, which can be used to aid in the probe operation. It is also easy to recognize the occurrence of a lesion site for which notification is not provided.

Figure 3:
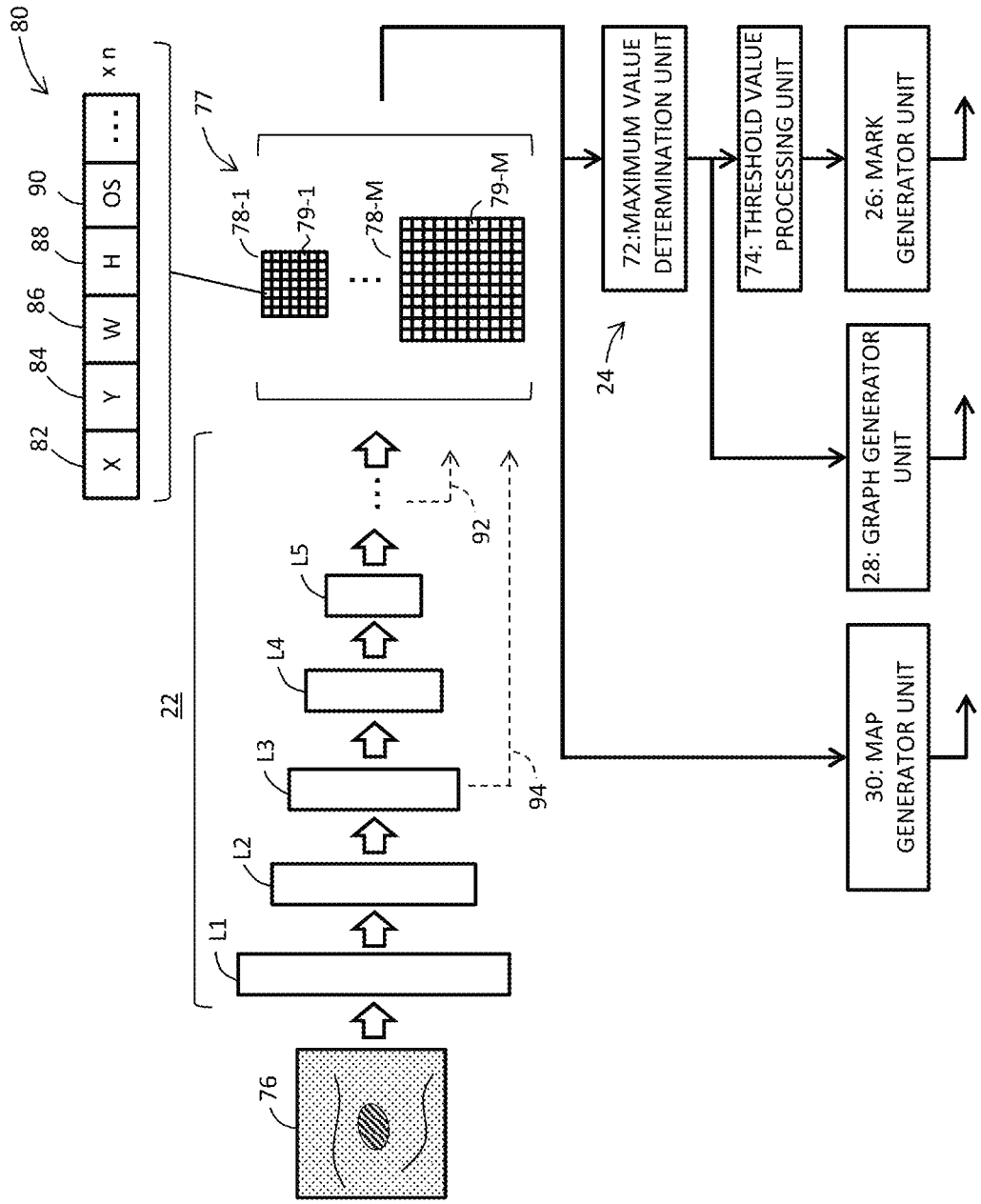
FIG. 3 is a conceptual illustration of detection processing and some associated steps of processing.

FIG. 3 schematically illustrates lesion site detection processing and some associated steps of processing. The lesion site detector unit 22 performs detection processing that consists of a plurality of detection steps. Referring to FIG. 3, the plurality of detection steps are performed in a plurality of layer sections that are successive in chronological order. The plurality of layer sections correspond to a learned network.

Specifically, FIG. 3 illustrates a plurality of layer sections including layer sections L1 to L5. Each layer section includes one or a plurality of convolution layers and optionally includes one or a plurality of pooling layers.

The layer section L1 is an input layer section, to which a tomographic image 76 serving as an input image is input. In the illustrated example structure, the plurality of layer sections includes a number M of output layer sections. A number M of output maps 78-1 to 78-M are output from the number M of output layer sections. M is an integer of 1 or greater, and M may be, for example, 2 or 3. The number M of output maps 78-1 to 78-M constitute output information 77. The output maps 78-1 to 78-M exhibit responses that are different from each other depending on the lesion site size. The output map 78-1 gives a large response to a lesion site having a large size, and therefore tends to show a result of detection of a lesion site having a large size. The output map 78-M gives a large response to a lesion site having a small size, and therefore tends to show a result of detection of a lesion site having a small size. Each of the output maps 78-1 to 78-M is composed of a plurality of cells 79-1 to 79-M that are arrayed two-dimensionally. Each of the cells 79-1 to 79-M has cell information that is associated with specific coordinates.

An example of cell information is given in the upper right of FIG. 3. The illustrated cell information 80 includes, for example, an X coordinate 82 and a Y coordinate 84 that identify center coordinates of a detected lesion site, information 86 that represents a horizontal width W of the detected lesion site, information 88 that represents a height (vertical width) H of the detected lesion site, an object score (OS) 90 that represents a probability that the lesion site falls under a specific class, and others. A number n of sets of cell information corresponding to a number n of classes may be generated for each cell.

The postprocessor unit 24 includes a maximum value determination unit 72 and a threshold value processing unit 74. The maximum value determination unit 72 identifies, for each display frame, a maximum object score in the output information 77 (that is, the plurality of output maps 78-1 to 78-M) as a maximum value. The threshold value processing unit 74 compares the identified maximum value with a threshold value. When the maximum value exceeds the threshold value, the mark generator unit 26 generates a mark. When the maximum value does not exceed the threshold value, no mark is generated. Instead of the maximum value determination, processing to determine a number K of highest object scores may be performed. In that case, a maximum number K of marks are generated simultaneously based on the number K of highest object scores. K is an integer of 2 or greater. Note that a graph is generated by referring to maximum values.

The graph generator unit 28 renders a maximum value for each display frame in the form of a bar and does this repeatedly, thereby generating a graph. Instead of a graph that shows a plurality of maximum values in chronological order, a graph that shows a plurality of average values in chronological order may be generated. A graph that shows maximum values may be subjected to moving average processing and other processing. The generated graph may also include a bar that represents a maximum value that does not satisfy the mark display condition.

In the example shown in FIG. 3, the output information 77 (that is, the plurality of output maps 78-1 to 78-M) is transmitted to the map generator unit 30 without being processed. In an embodiment, the map generator unit 30 generates a two-dimensional map based on the output information 77. Specifically, an object score; that is, a lesion site probability retrieved from each cell, is converted to a color. Colors obtained by the conversion are mapped in a two-dimensional space. The plurality of output maps 78-1 to 78-M have sizes that are different from each other, but they have a common coordinate system. The colors are mapped to the common coordinate system. Part of the output information 77 may serve as a target to be mapped.

When the output information 77 includes information (first information) that satisfies the mark display condition and information (second information) that does not satisfy the mark display condition, the mark generator unit 26 generates a mark based only on the information (first information) that satisfies the mark display condition (a maximum value condition and a threshold value condition). In that case, however, the map generator unit 30 generates a two-dimensional map based on both the information (first information) that satisfies the mark display condition and the information (second information) that does not satisfy the mark display condition. The graph generator unit 28 generates a graph based only on information that satisfies the maximum value condition.

Note that the plurality of output maps 78-1 to 78-M may be generated using feature maps 92 and 94 that are retrieved from some points during the detection processing.

FIG. 4 illustrates a first generation example of the two-dimensional map. Referring to intermediate information 100, in the illustrated example, a lesion site is detected at each of two coordinate points 102 and 104. In practical cases, lesion sites are detected at, for example, tens or hundreds of coordinate points in one display frame.

The lesion site probability at the coordinate point 102 is (0.8), and the lesion site probability at the coordinate point 104 is (0.4). The size of the lesion site detected at the coordinate point 102 is indicated by reference numeral 102A, and the size of the lesion site detected at the coordinate point 104 is indicated by reference numeral 104A.

In the first generation example, lesion site probabilities are converted to color codes. For example, the lesion site probability (0.8) at the coordinate point 102 is converted to a color code (204), and the lesion site probability (0.4) at the coordinate point 104 is converted to a color code (120). Reference numeral 106 denotes information obtained after the conversion. A two-dimensional map 108 is generated by mapping a color (an R value, a G value, and a B value) corresponding to each color code in a two-dimensional space. Scale-down processing and scale-up processing may be performed in the process of generating the two-dimensional map 108. Interpolation processing or smoothing processing may be applied after the color mapping.

FIG. 5 illustrates a second generation example of the two-dimensional map. The intermediate information 100, which is already described, is processed as follows. A local area 102B having certain dimensions is defined based on the size 102A that is identified at the coordinate point 102, and similarly, a local area 104B having certain dimensions is defined based on the size 104A that is identified at the coordinate point 104. The local areas 102B and 104B may be generated by, for example, scaling down the sizes 102A and 104A.

The lesion site probability (0.8) at the coordinate point 102 is converted to a color code (204), and the color code is assigned to the entire local area 102B. Similarly, the lesion site probability (0.4) at the coordinate point 104 is converted to a color code (120), and the color code is assigned to the entire local area 104B. Based on information 110 configured as described above, a two-dimensional map 112 is generated by mapping a color (an R value, a G value, and a B value) corresponding to each color code in a two-dimensional space.

In the second generation example, the sizes 102A and 104A may be used as the local areas 102B and 104B without being processed.

Figure 6:
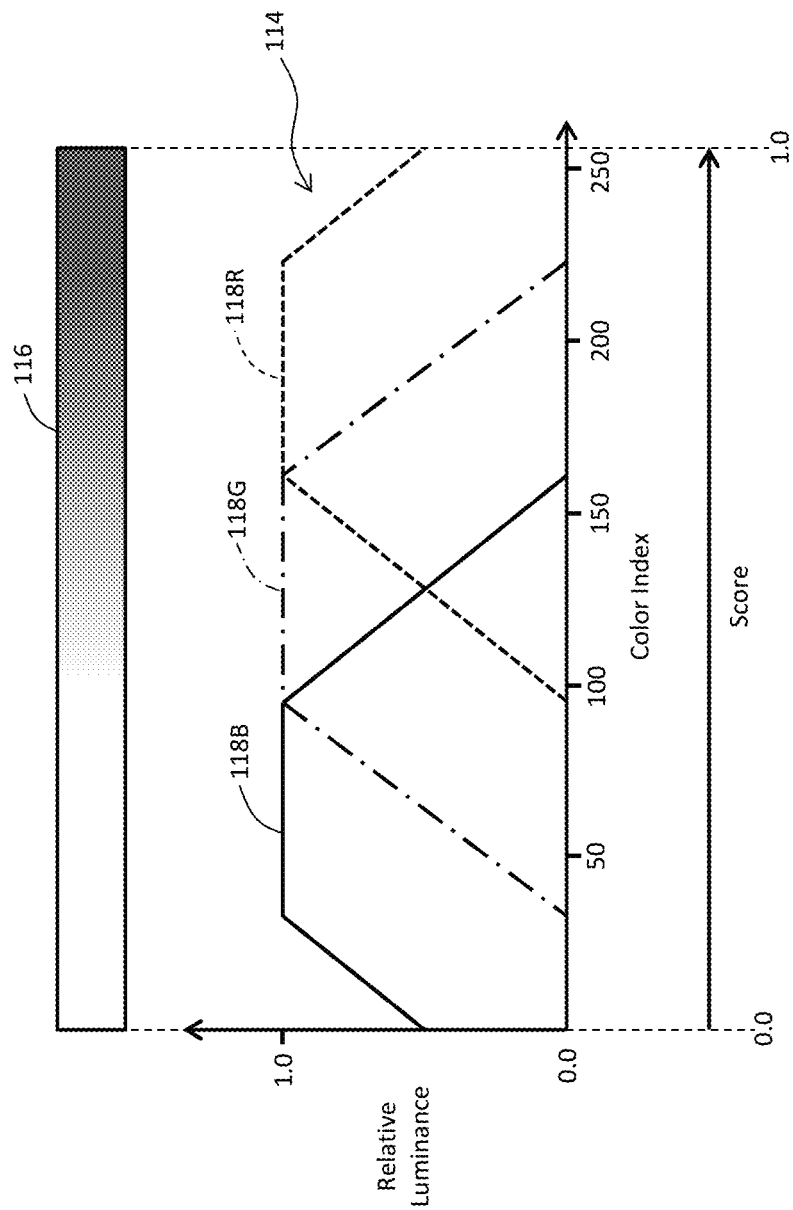
FIG. 6 is an illustrative diagram of color conversion.

FIG. 6 illustrates an example of color conversion. Reference numeral 114 denotes a color conversion function set. Specifically, the color conversion function set 114 is composed of a B conversion function 118B, a G conversion function 118G, and an R conversion function 118R. The horizontal axis represents the color index, which corresponds to the lesion site score. The vertical axis represents the relative luminance. FIG. 6 illustrates a color bar 116 that expresses colors defined by respective color indices. The color conversion function set 114 illustrated in FIG. 6 is given merely by way of example, and various types of color conversion function sets; that is, various types of color bars, may be used. The lesion site score can also be expressed by grayscale.

Figure 7:
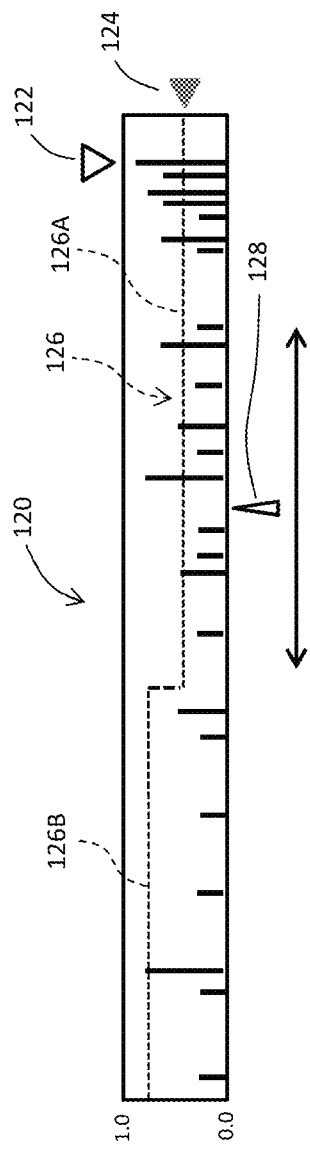
FIG. 7 illustrates a modification example of a graph.

FIG. 7 illustrates a modification example of a graph. A graph 120 is composed of a plurality of bars that represent lesion site probabilities. An index 122 represents the current time. There is a step in a threshold value line 126. The step represents a change in threshold value. A portion 126B, which is temporally older than the step, indicates a relatively high threshold value, and a portion 126A, which is temporally newer than the step, indicates a relatively low threshold value. An index 124 may be moved vertically to change the current threshold value. A change in threshold value changes the form of the threshold value line 126.

A tomographic image, a two-dimensional map, and a graph may be generated based on, for example, a frame data array that is stored in a cine memory, and they may be displayed. In that case, these images may be displayed in the form of a still-frame image associated with a past specific time, rather than in the form of a video image. In that case, the past specific time may be specified by an element 128. The element 128 is a mark that moves along the horizontal axis of the graph 120. For example, the past specific point in time at which a lesion site is detected may be specified by the element 128.

Figure 8:
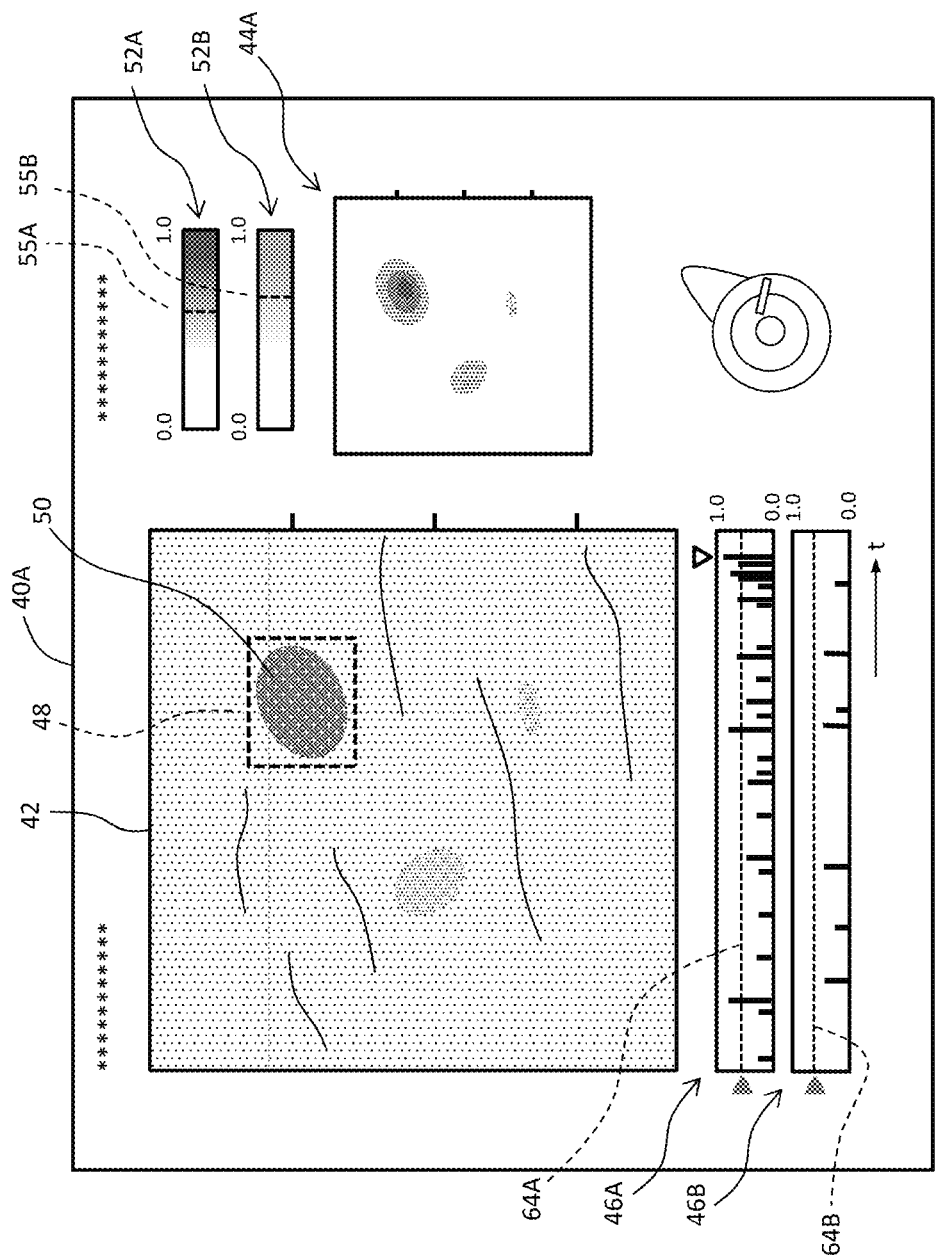
FIG. 8 illustrates an alternative example of a display image.

FIG. 8 illustrates an alternative example of a display image. A display image 40A includes a tomographic image 42, a two-dimensional map 44A, graphs 46A and 46B, and others. The tomographic image 42 includes a lesion site 50, and a mark 48 that provides notification thereof is superimposed. In this alternative example, two types of lesion sites (for example, a tumor site and a non-tumor site) are to be detected, and a lesion site probability; that is, a lesion site score, is calculated for each lesion site.

In the two-dimensional map 44A, for example, a first lesion site probability is expressed by the luminance of a blue-based hue, and a second lesion site probability is expressed by the luminance of a red-based hue. A relationship between the first lesion site probability and the luminance of the blue-based hue is expressed by a first color bar 52A, and a relationship between the second lesion site probability and the luminance of the red-based hue is expressed by a second color bar 52B. Lines 55A and 55B each representing a threshold value are indicated on the respective color bars 52A and 52B.

A first two-dimensional map representing distribution of first lesion site probabilities and a second two-dimensional map representing distribution of second lesion site probabilities may be separately generated and displayed. Although a first lesion site and a second lesion site are identified on the tomographic image 42 using the same mark 48 without being distinguished from each other, different markers may be displayed depending on the types of the lesion sites.

The first graph 46A represents temporal change of the first lesion site probabilities (maximum values). The second graph 46B represents temporal change of the second lesion site probabilities (maximum values). The first graph 46A includes a line 64A serving as a display element that represents a threshold value, and the second graph 46B includes a line 64B serving as a display element that represents a threshold value.

With the above-described embodiments, as inspection assistance information, a two-dimensional map and a graph are displayed in addition to a mark. The two-dimensional map and the graph are displayed regardless of whether or not the mark is displayed. As such, the inspector can obtain more detailed information regarding a current inspection target through the observation of these items of information that are displayed. This enables assistance in careful examination of a lesion site for which notification is provided through mark display, or enables verification of adequacy of mark display. Also, the current inspection target can be evaluated under circumstances where no mark is displayed.

The invention claimed is:

1. An ultrasound diagnostic apparatus comprising:
 a detector unit configured to perform detection processing for detecting a lesion site in an ultrasound image;
 a mark generator unit configured to generate a mark based on output information from the detector unit, the mark providing notification of the lesion site;
 a reference information generator unit configured to generate reference information based on the output information as inspection assistance information that is different from the mark, the reference information representing at least one of spatial distribution of lesion site probabilities and temporal change of lesion site probabilities; and
 a display configured to display the ultrasound image, the mark, and the reference information in real time,
 wherein the reference information generator unit includes a graph generator unit configured to generate, as the reference information, a graph that represents the temporal change of lesion site probabilities,
 wherein the graph generator unit identifies, for each frame, a representative value of lesion site probabilities in the frame, and wherein the graph generator unit generates the graph based on a plurality of representative values identified from a plurality of frames.

2. The ultrasound diagnostic apparatus according to claim 1, wherein the representative value for each of the frames is a maximum value.

3. The ultrasound diagnostic apparatus according to claim 1, wherein the reference information generator unit comprises a map generator unit configured to generate a two-dimensional map that represents the spatial distribution of lesion site probabilities, and wherein the reference information includes the two-dimensional map and the graph.

4. The ultrasound diagnostic apparatus according to claim 1, wherein the mark is displayed on the ultrasound image, and wherein the reference information is displayed in the vicinity of the ultrasound image.

5. The ultrasound diagnostic apparatus according to claim 1, wherein the reference information generator unit includes a map generator unit configured to generate, as the reference information, a two-dimensional map that represents the spatial distribution of lesion site probabilities.

6. The ultrasound diagnostic apparatus according to claim 5, wherein when the output information includes first information that satisfies a mark display condition and second information that does not satisfy the mark display condition, the mark generator unit generates the mark based on the first information, and the map generator unit generates the two-dimensional map based on the first information and the second information.

7. An ultrasound image processing method comprising:
performing detection processing for detecting a lesion site in an ultrasound image;
generating a mark based on output information that represents a result of execution of the detection processing, the mark providing notification of the lesion site;
generating reference information based on the output information as inspection assistance information that is different from the mark, the reference information representing at least one of spatial distribution of lesion site probabilities and temporal change of lesion site probabilities; and
displaying the ultrasound image, the mark, and the reference information in real time,
the reference information being generated as a graph that represents the temporal change of lesion site probabilities,
the mark being generated when the output information satisfies a mark display condition,
the mark display condition including a condition that requires that a lesion site probability identified from the output information exceeds a threshold value, and
the graph including a display element that represents the threshold value.

8. The ultrasound image processing method according to claim 7, further comprising changing the display element in accordance with a change in the threshold value.

9. The ultrasound image processing method according to claim 7, wherein the mark is displayed on the ultrasound image, and
the reference information is displayed in the vicinity of the ultrasound image.

10. The ultrasound image processing method according to claim 7, wherein
a two-dimensional map that represents the spatial distribution of lesion site probabilities is generated as the reference information.

11. The ultrasound image processing method according to claim 10, wherein
when the output information includes first information that satisfies a mark display condition and second information that does not satisfy the mark display condition, the mark is generated based on the first information, and the two-dimensional map is generated based on the first information and the second information.

12. The ultrasound image processing method according to claim 7, wherein
the representative value for each of the frames is a maximum value.

13. The ultrasound image processing method according to claim 7, further comprising:
generating a two-dimensional map that represents the spatial distribution of lesion site probabilities; and
generating the graph that represents the temporal change of lesion site probabilities,
wherein the reference information includes the two-dimensional map and the graph.

14. A non-transitory storage medium storing a program executable by an information processing apparatus, the program comprising:
a function of performing detection processing for detecting a lesion site in an ultrasound image;
a function of generating a mark based on output information that represents a result of execution of the detection processing, the mark providing notification of the lesion site;
a function of generating reference information based on the output information as inspection assistance information that is different from the mark, the reference information representing at least one of spatial distribution of lesion site probabilities and temporal change of lesion site probabilities, the reference information being generated as a graph that represents the temporal change of lesion site probabilities; and
a function of displaying the ultrasound image, the mark, and the reference information in real time; and
a function of identifying, for each frame, a representative value of lesion site probabilities in the frame,
the graph being generated based on a plurality of representative values identified from a plurality of frames.

15. The non-transitory storage medium according to claim 14, wherein
the mark is displayed on the ultrasound image, and
the reference information is displayed in the vicinity of the ultrasound image.

16. The non-transitory storage medium according to claim 14, wherein
a two-dimensional map that represents the spatial distribution of lesion site probabilities is generated as the reference information.

17. The non-transitory storage medium according to claim 16, wherein
when the output information includes first information that satisfies a mark display condition and second information that does not satisfy the mark display condition, the mark is generated based on the first information, and the two-dimensional map is generated based on the first information and the second information.

18. The non-transitory storage medium according to claim 14, wherein
the representative value for each of the frames is a maximum value.

19. The non-transitory storage medium according to claim 14, further comprising:
a function of generating a two-dimensional map that represents the spatial distribution of lesion site probabilities; and
a function of generating the graph that represents the temporal change of lesion site probabilities,
wherein the reference information includes the two-dimensional map and the graph.

* * * * *